(12) United States Patent
Greiner-Stoeffele et al.

(10) Patent No.: US 12,234,491 B2
(45) Date of Patent: *Feb. 25, 2025

(54) **METHODS OF RECOMBINANTLY PRODUCING NEUTRAL PROTEASE ORIGINATING FROM *PAENIBACILLUS POLYMXA***

(71) Applicant: Roche Diagnostics Operations, Inc., Indianapolis, IN (US)

(72) Inventors: Thomas Greiner-Stoeffele, Soemmerda (DE); Stefan Schoenert, Leipzig (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/057,800

(22) Filed: Nov. 22, 2022

(65) Prior Publication Data

US 2024/0132866 A1    Apr. 25, 2024
US 2024/0228999 A9    Jul. 11, 2024

Related U.S. Application Data

(63) Continuation of application No. 17/386,106, filed on Jul. 27, 2021, now Pat. No. 11,542,489, which is a continuation of application No. 16/355,259, filed on Mar. 15, 2019, now abandoned, which is a continuation of application No. 15/334,658, filed on Oct. 26, 2016, now Pat. No. 10,526,594, which is a continuation of application No. 14/592,969, filed on Jan. 9, 2015, now abandoned, which is a continuation of application No. PCT/EP2013/064271, filed on Jul. 5, 2013.

(30) Foreign Application Priority Data

Jul. 9, 2012    (EP) .................................. 12175563

(51) Int. Cl.
| | |
|---|---|
| C12N 9/54 | (2006.01) |
| C07K 14/195 | (2006.01) |
| C12N 5/071 | (2010.01) |
| C12N 9/52 | (2006.01) |
| C12N 15/57 | (2006.01) |
| C12N 15/75 | (2006.01) |

(52) U.S. Cl.
CPC .............. *C12N 9/52* (2013.01); *C07K 14/195* (2013.01); *C12N 5/0602* (2013.01); *C12Y 304/24* (2013.01); *C12Y 304/24028* (2013.01); *C12N 2509/00* (2013.01)

(58) Field of Classification Search
None
See application file for complete search history.

(56) References Cited

U.S. PATENT DOCUMENTS

| | | | |
|---|---|---|---|
| 3,133,001 | A | 5/1964 | Muset et al. |
| 3,930,954 | A | 1/1976 | Irie |
| 4,304,966 | A | 12/1981 | Green et al. |
| 5,762,502 | A | 6/1998 | Bahn et al. |
| 5,830,741 | A | 11/1998 | Dwulet et al. |
| 10,526,594 | B2 | 1/2020 | Greiner-Stoeffele |
| 10,889,809 | B2 | 1/2021 | Greiner-Stoeffele |
| 2005/0054098 | A1 | 3/2005 | Mistry et al. |
| 2006/0269527 | A1 | 11/2006 | Nilsson et al. |
| 2010/0192985 | A1 | 8/2010 | Aehle et al. |

FOREIGN PATENT DOCUMENTS

| | | |
|---|---|---|
| EP | 2161333 B1 | 3/2010 |
| WO | 1998024889 A1 | 6/1998 |
| WO | 2011009613 A1 | 1/2001 |
| WO | 2009140343 | 11/2009 |
| WO | 2010105820 A1 | 9/2010 |

OTHER PUBLICATIONS

Honjo, et al., Cloning and expression of the gene for neutral protease of Bacillus amyloliquefaciens in Bacillus subtilis, Journal of Biotechnology, 1984, pp. 265-277, vol. 1.

Ikram-Ul-Haq and Mukhtar, Hamid, Studies on the Optimization of Protease Production by Bacillus Subtilis H-16, Proceedings of the Pakistan Congress of Zoology, 2004, pp. 67-75, vol. 24.

Mansfeld, et al., The propeptide is not required to produce catalytically active neutral protease from Bacillus stearothermophilus, Protein Expression and Purification, 2005, pp. 219-228, vol. 39.

Matta, Hittu and Punj, Vasu, Isolation and partial characterization of a thermostable extracellular protease of Bacillus polymyxa B-17, International Journal of Food Microbiology, 1998, pp. 139-145, vol. 42.

Murao, et al., JI-Amylases from Bacillus polymyxa No. 72, Agriculture, Biology and Chemistry, 1979, pp. 719-726, vol. 43, No. 4.

Ruf, et al., Structure of Genllyase, the neutral metalloprotease of Paenibacillus polymyxa, Acta Crystallographica Section D, 2013, pp. 24-31, vol. D69.

Stenn, et al., Dispase, a Neutral Protease From Bacillus Polymyxa, Is a Powerful Fibronectinase and Type V Collagenase, Journal of Investigative Dermatology, 1989, pp. 287-290, vol. 93.

Takekawa, et al., Proteases Involved in Generation of ~- and a-Amylases from a Large Amylase Precursor in Bacillus polymyxa, Journal of Bacteriology, Nov. 1991, pp. 6820-6825, vol. 173, No. 21.

(Continued)

*Primary Examiner* — David Steadman
(74) *Attorney, Agent, or Firm* — Taft Stettinius & Hollister LLP

(57) ABSTRACT

The present disclosure provides the sequence of a *Paenibacillus polymyxa* preproenzyme which is the precursor of a neutral protease, expression thereof in a transformed host organism, and methods for production of the neutral protease, by recombinant means. Further, use of the recombinantly produced neutral protease is disclosed in the field of cell biology, particularly for the purpose of tissue dissociation. The disclosure also includes blends with other proteases. Further disclosed are nucleotide sequences encoding the neutral protease.

3 Claims, 1 Drawing Sheet

Specification includes a Sequence Listing.

(56) References Cited

OTHER PUBLICATIONS

Twentyman, Peter R. and Yuhas, John M., Use of a Bacterial neutral protease for Disaggregation of Mouse Tumours and Multicellular Tumour Spheroids, Cancer Letters, 1980, pp. 225-228, vol. 9.
Wang, Lin-Fa and Devenish, Rodney J., Expression of Bacillus subtilis Neutral Protease gene (nprE) in *Saccharomyces cerevisiae*, Journal of General Microbiology, 1993, pp. 343-347, vol. 139.
UNIPROT:E3E6LO, Subname: Full=Bacillolysin, 2013, retrieved from EBI accession No. UNIPROT:E3E6LO, 1 page.
PCTEP2013064271, IPER, Jan. 13, 2015.

```
Seq-1   1   MKKVWFSLLGGAMLLGSVASGASAESSVSGPAQLTPTFHTEQWKAPSSVSGDDIVWSYLN
            MKKVW SLLGGAMLLGSVASGASAESSVSGP QLTPTFH EQWKAPSSVSGDDIVWSYLN
Seq-2   1   MKKVWVSLLGGAMLLGSVASGASAESSVSGPTQLTPTFHAEQWKAPSSVSGDDIVWSYLN

Seq-1  61   RQKKSLLGVDSSSVREQFRIVDRTSDKSGVSHYRLKQYVNGIPVYGAEQTIHVGKSGEVT
            RQKKSLLG D SSVREQFRIVDRTSDKSGVSHYRLKQYVNGIPVYGAEQTIHVGKSGEVT
Seq-2  61   RQKKSLLGADDSSVREQFRIVDRTSDKSGVSHYRLKQYVNGIPVYGAEQTIHVGKSGEVT

Seq-1 121   SYLGAVINEDQQEEATQGTTPKISASEAVYTAYKEAAARIEALPTSDDTISKDAEEPSSV
            SYLGAV+ EDQQ EATQGTTPKISASEAVYTAYKEAAARIEALPTSDDTISKD EE SSV
Seq-2 121   SYLGAVVTEDQQAEATQGTTPKISASEAVYTAYKEAAARIEALPTSDDTISKDVEEQSSV

Seq-1 181   SKDTYAEAANNDKTLSVDKDELSLDKASVLKDSKIEAVEAEKSSIAKIANLQPEVDPKAE
            SKDTYAEAANN+KTLS DKDELSLDKAS LKDSKIEAVEAEKSSIAKIANLQPEVDPKA+
Seq-2 181   SKDTYAEAANNEKTLSTDKDELSLDKASALKDSKIEAVEAEKSSIAKIANLQPEVDPKAD

Seq-1 241   LYYYPKGDDLLLVYVTEVNVLEPAPLRTRYIIDANDGSIVFQYDIINEATGTGKGVLGDS
            LY+YPKGDDL LVYVTEVNVLEPAPLRTRYIIDANDGSIVFQYDIINEATGTGKGVLGD+
Seq-2 241   LYFYPKGDDLQLVYVTEVNVLEPAPLRTRYIIDANDGSIVFQYDIINEATGTGKGVLGDT

Seq-1 301   KSFTTTASGSSYQLKDTTRGNGIVTYTASNRQSIPGTLLTDADNVWNDPAGVDAHAYAAK
            KSFTTTASGSSYQLKDTTRGNG+VTYTASNRQSIPGT+LTDADNVWNDPAGVDAH YAAK
Seq-2 301   KSFTTTASGSSYQLKDTTRGNGVVTYTASNRQSIPGTILTDADNVWNDPAGVDAHTYAAK

Seq-1 361   TYDYYKSKFGRNSIDGRGLQLRSTVHYGSRYNNAFWNGSQMTYGDGDGDGSTFIAFSGDP
            TYDYYK+KFGRNSIDGRGLQLRSTVHYGSRYNNAFWNGSQMTY GDGDGSTFIAFSGDP
Seq-2 361   TYDYYKAKFGRNSIDGRGLQLRSTVHYGSRYNNAFWNGSQMTY--GDGDGSTFIAFSGDP

Seq-1 421   DVVGHELTHGVTEYTSNLEYYGESGALNEAFSDVIGNDIQRKNWLVGDDIYTPNICGDAL
            DVVGHELTHGVTEYTSNLEYYGESGALNEAFSDVIGNDIQRKNWLVGDDIYTPNI GDAL
Seq-2 419   DVVGHELTHGVTEYTSNLEYYGESGALNEAFSDVIGNDIQRKNWLVGDDIYTPNIAGDAL

Seq-1 481   RSMSNPTLYDQPHHYSNLYKGSSDNGGVHTNSGIINKAYYLLAQGGTFHGVTVNGIGRDA
            RSMSNPTLYDQP HYSNLY GSSDNGGVHTNSGIINKAYYLLAQGGTFHGVTVNGIGRDA
Seq-2 479   RSMSNPTLYDQPDHYSNLYTGSSDNGGVHTNSGIINKAYYLLAQGGTFHGVTVNGIGRDA

Seq-1 541   AVQIYYSAFTNYLTSSSDFSNARAAVIQAAKDLYGANSAEATAAAKSFDAVG--
            AVQIYYSAFTNYLTSSSDFSNARAAVIQAAKD YGANSAEATAAAKSFDAVG
Seq-2 539   AVQIYYSAFTNYLTSSSDFSNARAAVIQAAKDQYGANSAEATAAAKSFDAVGVN
```

METHODS OF RECOMBINANTLY PRODUCING NEUTRAL PROTEASE ORIGINATING FROM *PAENIBACILLUS POLYMXA*

RELATED APPLICATIONS

This application is a continuation of U.S. application Ser. No. 17/386,106 filed Jul. 27, 2021, issued as U.S. Pat. No. 11,542,489, which is a continuation of U.S. application Ser. No. 16/355,259 filed Mar. 15, 2019, which is a continuation of U.S. application Ser. No. 15/334,658 filed Oct. 26, 2016, issued as U.S. Pat. No. 10,526,594, which is a continuation of U.S. application Ser. No. 14/592,969 filed Jan. 9, 2015 now abandoned, which is a continuation of International Application No. PCT/EP2013/064271 filed Jul. 5, 2013, which claims priority to European Application No. 12175563.1 filed Jul. 9, 2012, the disclosures of which are hereby incorporated by reference in their entirety.

STATEMENT IN SUPPORT FOR FILING A SEQUENCE LISTING

A computer readable form of the Sequence Listing XML containing the file named-"3003372.0231 Sequence Listing.xml," which is 18,912 bytes in size (as measured by MICROSOFT WINDOWS® EXPLORER) and was created on Mar. 23, 2023, is provided herein and is herein incorporated by reference. This Sequence Listing consists of SEQ ID NOs: 1-8.

FIELD OF THE INVENTION

The present disclosure provides the sequence of a *Paenibacillus polymyxa* preproenzyme which is the precursor of a neutral protease, expression thereof in a transformed host organism, and methods for production of the neutral protease, by recombinant means. Further, use of the recombinantly produced neutral protease is disclosed in the field of cell biology, particularly for the purpose of tissue dissociation. The disclosure also includes blends with other proteases. Further disclosed are nucleotide sequences encoding the neutral protease, as well as fragments thereof.

The present invention is directed to the means for providing a recombinantly expressed and enzymatically active neutral protease from *Paenibacillus polymyxa*, also known as DISPASE®. Particularly, an amino acid sequence is provided which is suited for large-scale production by way of recombinant expression thereof, specifically and with particular advantage in transformed *Bacillus* species serving as a recombinant host strain. In a specific embodiment, recombinantly expressed *Paenibacillus polymyxa* neutral protease is secreted into liquid culture medium and purified therefrom.

BACKGROUND

From filtrates or supernatants of *Paenibacillus polymyxa* cultures (*P. polymyxa*; formerly also known as *Bacillus polymyxa* or *B. polymyxa*, all these taxonomic names are used synonymously herein), a neutral protease was isolated and characterized. In the more recent literature the neutral protease is often referred to as "DISPASE®", which is a registered trademark of Godo Shusei Co., Ltd., Tokyo, Japan. Owing to fibronectinase and type IV collagenase proteolytic activity, technical utility of DISPASE® is known particularly in the field of animal cell or tissue culture. Thus, dissociation of a tissue (including cell clumps or cell aggregates) into cell layers or even suspensions of single cells is frequently performed with the activity of this enzyme, either with DISPASE® alone or with DISPASE® as a component of blends, i.e. combined other proteolytic enzymes, specifically Collagenases, e.g. as disclosed in U.S. Pat. No. 5,830,741.

U.S. Pat. No. 3,930,954 discloses a neutral protease from *B. polymyxa* strain having the accession number ATCC™ 21993 (in the document also referred to as FERM-P No. 412). ATCC™ is the tradename of the American Type Culture Collection organization, a nonprofit, private global biological resource center that stores and catalogs biological material. The document particularly describes culturing of the bacterial strain under aerobic conditions in a complex liquid medium (culture broth) containing a carbon source, a nitrogen source and inorganic salts. The proteolytic activity present in the culture broth was monitored during cultivation, indicating the amount of neutral protease secreted by the cells into the liquid supernatant. When the maximum activity was reached the culture was harvested and particulate components including bacterial cells were separated from the supernatant by gel filtration, followed by concentration of the filtrate under reduced pressure. Following a not further specified fractionation step with isopropanol, a preparation representing 70% of the total proteolytic activity detected in the culture broth was obtained. Other methods of protease enrichment taught in U.S. Pat. No. 3,930,954 include salting out with ammonium sulfate and precipitation with methanol, ethanol and acetone, each resulting in a crude preparation. Subsequently, further purification steps were applied, ultimately leading to a purified preparation. By way of ultracentrifugation analysis a molecular weight of 35,900 Daltons (Da) was determined, and a number of other biochemical and biophysical parameters were examined. However, no unequivocal data were supplied clarifying whether the disclosed preparation contained a homogeneously purified single protease or a mixture of different proteins.

Stenn, K. S., et al., J. Invest. Dermatol. 93 (1989) 287-290 disclose an analysis of the substrate specificity of a neutral protease (=DISPASE®). In addition, a further biochemical characterization of the neutral protease is presented, using purified material derived from the culture filtrate of *B. polymyxa*, and making reference to U.S. Pat. No. 3,930,954. Notably, an SDS PAGE gel representing a sample of 600 µg of protein of a commercially available DISPASE® preparation is shown in the document. The Coomassie Blue-stained gel presents a thin major band migrating at 41 kDa, but also at least two faint bands migrating between 30 and 20 kDa, and a further faint band migrating between 20 and 14.4 kDa.

Using *B. polymyxa* strain 72 of Murao, S., et al. (Agric. Biol. Chem. 47 (1979) 941-947) the authors of Takekawa, S., et al., J. Bacteriology 173 (1991) 6820-6825 describe the cloning in *E. coli* of a genomic *B. polymyxa* DNA (SEQ ID NO:1) comprising a nucleotide sequence with an open reading frame apparently encoding the preproenzyme with 590 amino acids (SEQ ID NO:2; primary translation product, precursor molecule prior to secretion) of a neutral protease. Based on the amino acid composition the molecular weight of the conceptual mature (processed) secreted protein comprising 304 amino acids was calculated to be 32,477 Da. Neutral protease expressed in *E. coli* from a genomic *B. polymyxa* fragment and analyzed from the supernatant of disrupted transformed *E. coli* cells was found to migrate at about 35 kDa in SDS PAGE gels.

For comparison, Takekawa, S., et al. (supra) also purified *B. polymyxa* extracellular neutral protease from culture fluid. The N-terminal amino acid sequence of the purified neutral protease was determined. Notably, the first three amino acid residues in the *B. polymyxa* N-terminal sequence of Ala Thr Gly Thr Gly Lys Gly Val Leu Gly Asp Xaa Lys Ser Phe (SEQ ID NO:4) differ from the predicted amino acid sequence comprised in SEQ ID NO:2 at the positions 287-301 which were found to be Asn Glu Ala Thr Gly Lys Gly Val Leu Gly Asp Ser Lys Ser Phe (SEQ ID NO: 8). The reason for this discrepancy remained unclear and was not elucidated further.

The authors of the present disclosure set out to produce a transformed microbial host strain recombinantly expressing neutral protease from *Paenibacillus polymyxa*. Unexpectedly it turned out that the sequences disclosed by Takekawa, S., et al. (supra) were not suited to construct a suitable expression strain. Even more surprising, DNA isolated from *B. polymyxa* ATCC™ 21993 encoded an amino acid sequence of a primary translation product for a neutral protease which not only comprised 592 amino acids but also showed alterations at several position in the encoded polypeptide, when compared with previously published sequences. A further surprising effect was that *Bacillus amyloliquefaciens* is a particularly suited host organism for recombinant production of the neutral protease originating from *Paenibacillus polymyxa*.

SUMMARY

A first aspect of all embodiments as disclosed herein is a method for recombinantly producing a neutral protease, the method comprising the steps of (a) providing in an expression vector a DNA with a sequence encoding a preproenzyme according to SEQ ID NO:5, and transforming a host organism with the expression vector, thereby obtaining a transformed host organism, wherein the host organism is a gram-positive prokaryotic species; followed by (b) expressing the DNA in the transformed host organism, wherein the transformed host organism secretes the neutral protease; followed by (c) isolating the secreted neutral protease; thereby recombinantly producing the neutral protease. In one embodiment, the host organism is *Bacillus amyloliquefaciens*.

A second aspect of all embodiments as disclosed herein is a neutral protease obtained by performing a method for recombinantly producing a neutral protease as disclosed herein.

A third aspect of all embodiments as disclosed herein is a method of isolating living cells from animal tissue in vitro, comprising the steps of (a) providing a recombinantly produced neutral protease obtained by performing a method for recombinantly producing a neutral protease as disclosed herein, and (b) incubating the tissue in vitro with the neutral protease of step (a), wherein protein components of the extracellular matrix of the tissue are proteolytically degraded, and wherein a layer of cells or a suspension of individual living cells is obtained, thereby isolating living cells from animal tissue in vitro.

A fourth aspect of all embodiments as disclosed herein is the use of a neutral protease obtained by performing a method for recombinantly producing a neutral protease as disclosed herein, the use of the neutral protease being the isolation of living cells from animal tissue in vitro.

A fifth aspect of all embodiments as disclosed herein is a kit of parts comprising in a sealed compartment a lyophilizate of a neutral protease obtained by performing a method for recombinantly producing a neutral protease as disclosed herein.

A sixth aspect of all embodiments as disclosed herein is a method for making a blend of a plurality of proteases, comprising the steps of (a) providing a recombinantly produced neutral protease obtained by performing a method for recombinantly producing a neutral protease as disclosed herein, and (b) mixing the neutral protease of step (a) with a further protease.

A seventh aspect of all embodiments as disclosed herein is a nucleotide sequence encoding a polypeptide comprising the amino acid sequence of position 289 to position 592 of SEQ ID NO:5, the nucleotide sequence being selected from the group consisting of (a) a nucleotide sequence having the sequence of position 898 to position 1811 in SEQ ID NO:6; (b) nucleotide sequences derived from the nucleotide sequence of position 898 to position 1811 of SEQ ID NO:6 as a result of the degenerated code.

An eighth aspect of all embodiments as disclosed herein is a vector containing a nucleotide sequence as disclosed herein.

A ninth aspect of all embodiments as disclosed herein is a transformed prokaryotic Gram-positive host organism containing at least one vector as disclosed herein.

BRIEF DESCRIPTION OF THE FIGURES

FIG. 1 Alignment of the published amino acid sequence of Takekawa, S., et al., J. Bacteriology 173 (1991) 6820-6825 (SEQ ID NO:3; "Seq-1" in the FIGURE) with the amino acid sequence originating from *P. polymyxa* ATCC™ 21993 (SEQ ID NO:5; "Seq-2" in the FIGURE), disclosed herein.

DETAILED DESCRIPTION

DISPASE® (=neutral protease originating from *Paenibacillus polymyxa*, *P. polymyxa*) is a metalloenzyme which is classified as an amino-endo peptidase capable of cleaving fibronectin, collagen IV, and collagen I, but the latter apparently to a lesser extent. *P. polymyxa* neutral protease is useful for tissue dissociation (=disaggregation) and particularly for subcultivation procedures since it does not damage cell membranes. Since *P. polymyxa* neutral protease according to the present disclosure can be produced from a bacterial source, it is free of *mycoplasma* and animal virus contamination. It is very stable with respect to temperature, pH and interference by serum components. *P. polymyxa* neutral protease activity is greatly reduced by dilution, allowing suspension cultures to grow without difficulty. *P. polymyxa* neutral protease can even be added to cell suspension cultures to prevent unwanted cell clumping.

*P. polymyxa* neutral protease prepared recombinantly according to the present disclosure is useful to prepare many types of cells for culture. Thus, *P. polymyxa* neutral protease as provided herewith is a rapid, effective, but gentle agent for separating even cell layers, that is to say intact epidermis from the dermis and intact epithelial sheets in culture from the substratum. In both cases, it affects separation by cleaving extracellular matrix proteins in the basement membrane zone region while preserving the viability of the epithelial cells. *P. polymyxa* neutral protease according to the present disclosure and used as sole protease is useful for detaching epidermal cells as confluent, intact sheets from the surface of culture dishes without dissociating the cells. Such a procedure paves the way for the use for culture and even transplantation of skin epithelial cell sheets detached from the culture substrate by *P. polymyxa* neutral protease. Also, *P. polymyxa* neutral protease is useful for the harvest and transfer of normal diploid cells and cell lines. Further applications for tissue dissociation make use of blends of *P. polymyxa* neutral protease and a further protease such as a collagenase.

According to the surprising findings of the authors of the present disclosure, there is provided a method for recombinantly producing a neutral protease, the method comprising the steps of (a) providing in an expression vector a DNA with a sequence encoding a preproenzyme according to SEQ ID NO:5, and transforming a host organism with the expression vector, thereby obtaining a transformed host organism, wherein the host organism is a gram-positive prokaryotic species; followed by (b) expressing the DNA in the transformed host organism, wherein the transformed host organism secretes the neutral protease; followed by (c) isolating the secreted neutral protease; thereby recombinantly producing the neutral protease. More specifically, the DNA sequence originates from *Paenibacillus polymyxa* ATCC™ 21993.

The sequence encoding the preproenzyme according to SEQ ID NO:5 can be expressed in any suitable host organism known to the skilled person. A particular host organism is a gram-positive bacterium, specifically a species selected from the group consisting of *Bacillus, Clostridium, Lactococcus, Lactobacillus, Staphylococcus* and *Streptococcus*. A very suitable way of recombinantly producing the neutral protease encoded by SEQ ID NO:5 makes use of the species *Bacillus amyloliquefaciens* as transformed host organism.

In a specific embodiment, the step of expressing the DNA in the transformed host organism is performed by culturing the transformed host organism in a liquid medium, wherein the transformed host organism secretes the neutral protease into the liquid medium. Subsequently, the secreted neutral protease can be isolated from the liquid medium.

Further advantage can be achieved by using in any of the methods for recombinantly producing a neutral protease a host organism which is deficient for extracellular proteases. Examples for *B. amyloliquefaciens* extracellular proteases are Npr and Apr, well known to the skilled person.

In an exemplary workflow for tissue dissociation, *P. polymyxa* neutral protease recombinantly produced according to the present disclosure is provided as a lyophilizate. In a first step, the lyophilizate is dissolved in a physiologically suited buffer, e.g. in PBS (phosphate buffered saline) which is free of $Mg^{2+}$ and $Ca^{2+}$ ions. The *P. polymyxa* neutral protease solution is then sterilized, e.g. by way of filtration through a filter membrane (e.g. 0.22 µm pore size). A sample of living tissue is obtained, i.e. removed from the animal. Alternatively, a culture vessel with adherent cells or a culture vessel with cell aggregates is provided (the cells are also referred to as "tissue" herein). In a particular embodiment, the tissue is fragmented by mechanical means (e.g. using scissors or a scalpel), and the fragments are washed in sterile PBS. Subsequently, the fragments are incubated in pre-warmed *P. polymyxa* neutral protease solution, whereby the fragments are covered by the solution. Incubation with *P. polymyxa* neutral protease is typically performed at physiological temperature, particularly at 37° C.

The time needed for the desired (i.e. the degree or extent of) tissue dissociation is usually determined empirically, wherein typically *P. polymyxa* neutral protease concentration in the solution and/or incubation time are varied. Incubation time in *P. polymyxa* neutral protease solution can be several hours without adverse effects on the cells. The incubated tissue can optionally be agitated gently. If necessary, dispersed cells can be separated from still existing aggregates by way of passing the obtained cell suspension through a sterile mesh or grid. Decanting is also a method to obtain dissociated cells. Further techniques are known to the skilled person, particularly to remove cell layers which are detached from tissue underneath by incubation with *P. polymyxa* neutral protease. Fresh DISPASE® solution may be added if further disaggregation is desired.

Dissociated cells or cell layers can be pelleted, enzyme solution can be removed by decanting, or the *P. polymyxa* neutral protease solution is diluted with cell culture medium, in order to inhibit further proteolytic activity. Other methods to do so are possible. Cells obtained by the above workflow can be plated and cultured using standard procedures.

Thus, the present disclosure further provides a method to isolate living cells from animal tissue in vitro, comprising the steps of (a) providing a recombinantly produced neutral protease obtained by performing a method for recombinantly producing a neutral protease as disclosed herein, and (b) incubating the tissue in vitro with the neutral protease of step (a), wherein protein components of the extracellular matrix of the tissue are proteolytically degraded, and wherein a cell layer or a suspension of individual cells is obtained. Specifically, the animal tissue origins from a vertebrate animal, more specifically from an animal species selected from mouse, guinea pig, hamster, rat, dog, sheep, goat, pig, bovine, horse, a primate species, and human.

In another embodiment, a method to isolate living cells from animal tissue in vitro comprises the use of a protease blend which includes a *P. polymyxa* neutral protease recombinantly produced as disclosed herein. The blend may, by way of example, comprise a further neutral protease such as thermolysin. Further, blends of *P. polymyxa* neutral protease with a collagenase provide great advantage for tissue dissociation.

In a specific embodiment, *P. polymyxa* neutral protease recombinantly produced as disclosed herein or a blend of proteases including *P. polymyxa* neutral protease recombinantly produced as disclosed herein is provided as a lyophilizate, i.e. as a freeze-dried preparation. Such a preparation can be stored for an extended amount of time.

Further, there is provided a kit of parts comprising in a sealed compartment, such as a bottle, a lyophilizate of a neutral protease obtained by performing a method for recombinantly producing a neutral protease, as disclosed herein. The kit may contain in a separate sealed compartment a lyophilized preparation of a collagenase. The kit may also contain in a separate sealed compartment a lyophilized preparation of a thermolysin. Another embodiment is a kit comprising in a sealed compartment, such as a bottle, a lyophilizate of a neutral protease obtained by performing a method for recombinantly producing a neutral protease, as disclosed herein, wherein the neutral protease is blended with a further protease such as (but not limited to) a collagenase and/or thermolysin.

The following examples and the sequence listing are provided to aid the understanding of the present invention, the true scope of which is set forth in the appended claims. It is understood that modifications can be made in the procedures set forth without departing from the spirit of the teachings disclosed herein.

Example 1

Construction of Expression Constructs (DNA)

Using the polymerase chain reaction (PCR) and several synthesized single- and/or double-stranded DNA oligonucleotides representing subsequences of the desired coding and non-coding genomic DNA strands, artificial gene sequences were generated. To start with, partially overlapping pairs of oligonucleotides representing fragments of opposite strands were hybridized with template DNA, and double-stranded DNA molecules were generated by polymerase-mediated strand-extension, and subsequent PCR amplification. Further DNA molecules were created synthetically. All sequences of artificially generated DNAs were verified by sequencing.

Example 2

Expression Constructs Using Published Sequence Information

A first attempt to express *P. polymyxa* neutral protease was based on the disclosure of Takekawa, S., et al., J. Bacteriology 173 (1991) 6820-6825. In a first step, the nucleotide sequence of SEQ ID NO:1, specifically the subsequence of CDS (343) . . . (2115) corresponding to the open reading frame encoding SEQ ID NO:2 was adapted by changing the codon usage. While the encoded amino acid sequence remained unchanged, neutral mutations optimizing the open reading frame for expression in *Bacillus subtilis* were introduced. An artificial DNA with the reading frame encoding SEQ ID NO:2 was created and synthesized. It encoded the *P. polymyxa* amino acid sequence of the preproenzyme with 590 amino acids, i.e. including the signal sequence and the propeptide. In the expression construct a *B. subtilis*-specific ribosome binding site was introduced upstream of the open reading frame. The DNA construct was cloned in an expression vector which provides a growth phase-specific promoter driving transcription in *B. subtilis* in the stationary phase of growth in liquid culture. The resulting selectable and replication-competent expression plasmid was pLE2D01nprPp.

A derivative was constructed by fusing three Glycines and six Histidines to the C-terminus of the amino acid sequence of the preproenzyme resulting in an encoded polypeptide with 599 amino acids with six terminal Histidines. The resulting selectable and replication-competent expression plasmid was pLE2D01nprHisPp.

Transformed *B. subtilis* strains were generated and expression experiments under standard conditions were made; i.e. conditions were applied in case of other expression targets have shown to be permissive with expression and secretion of detectable quantities of target protein.

Surprisingly, both expression plasmids, pLE2D01nprPp and pLE2D01nprHisPp, lead to negative results. Both attempts to express and secrete *P. polymyxa* neutral protease were unsuccessful.

To exclude any negative impact of the promoter sequence, although such an effect was thought unlikely, the promoter in each of the two above plasmids was exchanged by another promoter driving expression dependent on the addition of a specific inductor compound to the culture. The resulting expression plasmids were designated pLE2E01nprPp and pLE2E01nprHisPp. Expression experiments were made including the step of addition of the inductor. As a result, these modifications did not lead to a change. Both further attempts to express and secrete *P. polymyxa* neutral protease were unsuccessful.

In a further attempt, the *B. subtilis* specific ribosome binding site was exchanged by the native *P. polymyxa* ribosome binding site of the originally described gene (SEQ ID NO:1). The resulting expression plasmids were designated pLE2D01nprRBSPp and pLE2D01nprRBSHisPp. Again, the negative results could not be reversed. Both additional attempts to express and secrete *P. polymyxa* neutral protease were unsuccessful.

In addition, mutation experiments were made altering/deleting amino acid positions relating to the sequence discrepancy shown in SEQ ID NO:3, i.e. by the N-terminal amino acid sequence of the native neutral protease isolated from *Paenibacillus polymyxa* culture supernatant.

Surprisingly and unexpectedly, none of the above straightforward attempts to express *P. polymyxa* neutral protease in *Bacillus subtilis* led to protease activity which was above background, compared to a *B. subtilis* control strain transformed with an "empty" expression vector, i.e. with a vector comprising the same features as described above but without any inserted desired coding sequence. Identical results were obtained, when *B. amyloliquefaciens* was used as expression host.

It is noted in this regard that the sequences published by Takekawa, S., et al., J. Bacteriology 173 (1991) 6820-6825 were cloned and selected in *E. coli*, that is to say in a microbial organism which was unrelated to *P. polymyxa*, taxonomically and in evolutionary terms. One may speculate that passage though such a distinct host might have lead to alterations of the foreign DNA. Also, Takekawa, S., et al. (supra) characterized neutral protease expression in *E. coli* using cellular extracts. However, positive clones were initially identified based on a halo on skim milk agar plates, hinting at some extracellular protease activity at an initial phase of the study.

The exact reason has not been found to explain why the published sequence of Takekawa, S., et al. (supra) does not lead to detectable expression of neutral protease, at least as far as the *B. subtilis* system is concerned. Nevertheless, a further attempt was made to elucidate whether the sequence information documented by Takekawa S. et al. (supra) might not represent the true *Paenibacillus polymyxa* gene.

Example 3

Sequencing Results for *Paenibacillus polymyxa* Strain ATCC™ 21993

Total genomic DNA isolated from *Paenibacillus polymyxa* strain ATCC™ 21993 was isolated and the gene encoding the neutral protease was amplified using PCR. The amplified DNA was sequenced. Surprisingly, several differences on the DNA sequence level were found, the differences giving rise to changes in the amino acid sequence which is encoded. The amino acid sequence of the neutral protease gene of the ATCC™ 21993 strain is given in SEQ ID NO:5.

On the amino acid sequence level an alignment with the published sequence of Takekawa, S., et al. (supra) is presented in FIG. 1. The alignment shows a number of amino acid exchanges and even a deletion and an insertion. 17 of the amino acid exchanges could be of higher-order structural relevance since in these cases the amino acids are not similar (size, charge) but differ significantly.

Notably, the amino acid sequence determined in the present study contained the N-terminus determined earlier by Takegawa S. et al. (supra). Thus positions 289 to 303 of SEQ ID NO:5 correspond to the previously determined N-terminal sequence of SEQ ID NO:4. According to the present sequencing data, following a proteolytic maturation process including N-terminal proteolytic processing during the course of secretion, the extracellular neutral protease derived from the ATCC™ 21993 strain is the polypeptide given by the amino acid sequence of SEQ ID NO: 5 from position 289 to position 592.

Example 4

Expression Constructs Using Published Sequence Information

The DNA encoding the neutral protease was isolated from *Paenibacillus polymyxa* strain ATCC™ 21993 as described in Example 3. Based on the amino acid sequence of SEQ ID NO:5, a DNA sequence for expression in *B. subtilis* encoding the neutral protease was devised and cloned in different expression vectors, in analogy to Example 2. The DNA sequence of a cloned fragment including the coding sequence of the of the neutral protease (preproenzyme) of said *Paenibacillus polymyxa* strain ATCC™ 21993 is presented as SEQ ID NO:6. An exemplary construct encoded the *P. polymyxa* amino acid sequence of the preproenzyme including the signal sequence and the propeptide. The DNA construct was cloned in an expression vector which provides a growth phase-specific promoter driving transcription in *B. subtilis* in the stationary phase of growth in liquid culture. The resulting selectable and replication-competent expression plasmid was pLE2D01DisnatPp.

It was further attempted to construct a derivative by fusing a tag sequence of three consecutive Glycines followed by six Histidines to the C-terminus of the amino acid sequence of the preproenzyme. Respective transformation experiments yielded clones which on milk agar plates produced halos indicative of protease secretion. Thus, recombinant production of the neutral protease is possible in *B. subtilis*.

Transformed *B. subtilis* strains were characterized further. Sequencing of expression plasmids surprisingly revealed that all these clones contained neutral protease-specific open reading frames in which the added Histidine tag was lost. In the particular *B. subtilis* expression system the His-tag structure appended to the C-terminus could have been incompatible with expression and/or secretion of the proteolytically active recombinant neutral protease enzyme. Thus, this attempt was not pursued further and no clones actively expressing a recombinant His-tagged neutral protease were generated in the *B. subtilis* system.

However, the expression plasmid pLE2D01DisnatPp was transformed into several *Bacillus* species, including not only *Bacillus subtilis*, but also *Bacillus amyloliquefaciens*. Control transformations were made with "empty" expression vectors, as described before.

Surprisingly, in liquid cultures transformed *Bacillus amyloliquefaciens* host strains secreted particularly high amounts of neutral protease into the medium while under the same conditions no significant neutral protease activities in the culture supernatant were observed with *Bacillus subtilis*. The effect did not seem to be dependent on the composition of the liquid medium. The reason for this unexpected observation was not elucidated.

Particular transformed *Bacillus subtilis* host strains used for transformation contained loss-of-function mutations in one or more endogenous genes encoding an extracellular (secreted) protease. Such strains are considered to be advantageous, particularly in the present case when the desired target protein to be recombinantly expressed and secreted is a protease itself. Particularly in the transformed *B. subtilis* host protease genes selected from AprE, NprE, Epr, and a combination thereof were mutated. In addition, strains were obtained in which all three of these genes were mutated.

With respect to *Bacillus amyloliquefaciens*, advantageous mutations in the host strain included the endogenous extracellular protease genes Npr and Apr. Respective transformants werde generated including one or both of the two aforementioned protease loss-of-function mutations.

Example 5

Determination of Proteolytic Activity in Liquid Medium

The ENZCHEK® Protease Assay Kits were used (Invitrogen, E6638). The direct fluorescence-based assay detects metallo-, serine, acid and sulfhydryl proteases. The assay kit contains casein derivatives that are labeled with the pH-insensitive greenfluorescent BODIPY® FL (E6638) dye, resulting in almost total quenching of the conjugate's fluorescence. Protease-catalyzed hydrolysis releases fluorescent BODIPY® FL dye-labeled peptides. The accompanying increase in fluorescence, which can be measured with a spectrofluorometer, minifluorometer or microplate reader, is proportional to protease activity.

Control experiments were made with samples in which no neutral protease was expressed ("null samples"). Additional controls were made with samples, including "null samples" to which a pre-determined amount of commercially available neutral protease (DISPASE®, Roche Diagnostics Manheim, Germany, Cat. No. 04942086001) was added.

The invention claimed is:

1. A method for recombinantly producing a neutral protease, the method comprising the steps of
   (a) providing in an expression vector a DNA with a sequence encoding a preproenzyme comprising the amino acid sequence of SEQ ID NO:5, and transforming a host organism with the expression vector, thereby obtaining a transformed host organism, wherein the host organism is a gram-positive prokaryotic species; followed by
   (b) expressing the DNA in the transformed host organism, wherein the transformed host organism secretes the neutral protease as a proteolytic processing product of said preproenzyme; followed by
   (c) isolating the secreted neutral protease;
   thereby recombinantly producing the neutral protease, and wherein the gram-positive prokaryotic species is *Bacillus amyloliquefaciens*.

2. The method according to claim 1, wherein the DNA comprises the sequence of position 34 to position 1896 of SEQ ID NO:6.

3. The method according to claim 1, wherein the host organism is deficient of an extracellular protease selected from Npr and Apr.

\* \* \* \* \*

SEQUENCE LISTING

```
Sequence total quantity: 8
SEQ ID NO: 1         moltype = DNA  length = 2418
FEATURE              Location/Qualifiers
misc_feature         1..2418
                     note = Paenibacillus polymyxa npr gene for extracellular
                      neutral protease, "extracellular neutral protease" genomic
                      sequence disclosed by Takekawa, S., Uozumi, N.,
                      Tsukagoshi, N. and Udaka, S. (J. Bacteriol. 172 (21),
                      6820-6825 (1991)) Genbank: D00861.1
source               1..2418
                     mol_type = genomic DNA
                     organism = Bacillus polymyxa 72
CDS                  343..2115
SEQUENCE: 1
gatcttctcg tccgtcattc tctgtgctaa tatcagagcc agatgatggg agttcgaaaa    60
atcatctttt gttttttttg cataaggcaa cttttttcca ttatccgctt ttatccacta   120
tcttttata cgacaggaag ggaggggttt gttaccttt taggctactt gcttcaaatg    180
```

```
cagtacccttt ttttcacgca cgcttcatga aaaacacttc ggtatttctc ttcatgttcc  240
attcttctat tccagacgac aacacgacct acataaatgg cgtaatgcct tattcaaagc  300
aggataattc gtcctgacat taatcgagga gagtgaattt ttatgaaaaa agtatggttt  360
tcgcttcttg gaggagctat gttattaggg tctgtggcgt ctggtgcatc tgcggagagt  420
tccgtttcgg gaccagcaca gcttacaccg accttccaca ccgagcaatg gaaagctcct  480
tcctcggtat caggggacga cattgtatgg agctatttga atcgacaaaa gaaatcgtta  540
ctgggtgtgg atagctccag tgtacgtgaa caattccgaa tcgttgatcg cacaagcgac  600
aagtccggtg tgagccatta tcgactgaag cagtatgtaa acgggattcc cgtatatgga  660
gctgagcaaa ctattcatgt gggcaaatca ggtgaggtca cctcttactt aggagcggtg  720
attaatgagg atcagcagga agaagctacg caaggtacaa ctccaaaaat cagcgcttct  780
gaagcggttt acaccgcata taagaagca gctgcacgta ttgaagccct ccctacctcc  840
gacgatacta tttctaaaga cgctgaggag ccaagcagtg taagtaaaga tacttacgcc  900
gaagcagcta acaacgacaa aacgcttct gttgataagg acgagctgag tcttgataag  960
gcatctgtcc tgaaagatag caaaattgaa gcagtggagg ccgaaaaaag ttccattgcc 1020
aaaatcgcta atctacagcc tgaagtagat cctaaagcag aactctacta ctaccctaaa 1080
ggggatgacc tgctgctagt ttatgtgaca gaagttaatg ttttagaacc tgccccactg 1140
cgtacccgct acattattga tgccaatgac ggcagcatcg tattccagta tgacatcatt 1200
aatgaagcga caggtaaagg tgtgcttggt gattccaaat cgttcactac taccgcttcc 1260
ggcagtagct accagttaaa agataccaca cgcggtaacg gtatcgtgac ttacacggcc 1320
tccaaccgcc aaagcatccc aggcacccctt tgacagatg ctgataatgt atggaatgat 1380
ccagccggtg tggatgccca tgcgtatgct gccaaaacct atgattacta taatccaaaa 1440
tttggacgca acagcattga cggacgtggt ctgcaactcc gttcgacagt ccattacggc 1500
agccgctaca acaacgcttt ctggaacggc tcccaaatga cttatggaga tggagatgta 1560
gacggtagca catttatcgc cttcagcggg gaccccgatg tagtagggca tgaacttaca 1620
catggtgtca cagagtatac ttcgaatttg gaatattacg gagagtccgg cgcattgaat 1680
gaggcttttct cggacgttat cggtaatgac attcaacgca aaaactggct tgtaggcgat 1740
gatatttata cgccaaacat ttgcggcgat gcccttcgct caatgtccaa tcctactctg 1800
tacgatcaac cacatcacta ttccaacctg tataaaggca gctccgataa cggcggcgtt 1860
catacaaaca gcgtattat caataaagcc tactacttgt tggcacaagg cggtactttc 1920
catggcgtta ctgtaaatgg aattgggcgc gatgctgcgg tgcaaattta ttatagtgcc 1980
tttacgaact acctgacttc ttcttccgac ttctccaacg cacgtgctgc tgtgatccaa 2040
gccgcaaaag atctgtacgg ggcgaactca gcagaagcaa ctgcagctgc caagtctttt 2100
gacgctgtag gctaaactaa atcatataca cgatcctcct cattctgtg ccatagacct 2160
ttgccattgt gcaactgtca cttggctctg ccataccatg gacgaaaaat aggggtgcag 2220
tgtacaagtc tgcacccctt ccccccttat ttatggcgcc ccctcaaagg gctccttttc 2280
tcttataaaa gtaatcctgt atctcttgct ttttcacag cttcttctcg attgttgact 2340
ccagcttgac atagagagtg gaggcgaatt cttactgtcc gtggataggt aagttctcag 2400
aattgtttat acgttctg                                               2418

SEQ ID NO: 2          moltype = AA  length = 590
FEATURE               Location/Qualifiers
source                1..590
                      mol_type = protein
                      organism = Bacillus polymyxa 72
SEQUENCE: 2
MKKVWFSLLG GAMLLGSVAS GASAESSVSG PAQLTPTFHT EQWKAPSSVS GDDIVWSYLN  60
RQKKSLLGVD SSSVREQFRI VDRTSDKSGV SHYRLKQYVN GIPVYGAEQT IHVGKSGEVT 120
SYLGAVINED QQEEATQGTT PKISASEAVY TAYKEAAARI EALPTSDDTI SKDAEEPSSV 180
SKDTYAEAAN NDKTLSVDKD ELSLDKASVL KDSKIEAVEA EKSSIAKIAN LQPEVDPKAE 240
LYYYPKGDDL LLVYVTEVNV LEPAPLRTRY IIDANDGSIV FQYDIINEAT GKGVLGDSKS 300
FTTTASGSSY QLKDTTRGNG IVTYTASNRQ SIPGTLLTDA DNVWNDPAGV DAHAYAAKTY 360
DYYKSKFGRN SIDGRGLQLR STVHYGSRYN NAFWNGSQMT YGDGDGDGST FIAFSGDPDV 420
VGHELTHGVT EYTSNLEYYG ESGALNEAFS DVIGNDIQRK NWLVGDDIYT PNICGDALRS 480
MSNPTLYDQP HHYSNLYKGS SDNGGVHTNS GIINKAYYLL AQGGTFHGVT VNGIGRDAAV 540
QIYYSAFTNY LTSSSDFSNA RAAVIQAAKD LYGANSAEAT AAAKSFDAVG             590

SEQ ID NO: 3          moltype = AA  length = 590
FEATURE               Location/Qualifiers
source                1..590
                      mol_type = protein
                      organism = Bacillus polymyxa 72
REGION                1..590
                      note = Preproenzyme with 590 amino acids according to
                      Takekawa S. et al. J. Bacteriology 173 (1991) 6820-6825
SEQUENCE: 3
MKKVWFSLLG GAMLLGSVAS GASAESSVSG PAQLTPTFHT EQWKAPSSVS GDDIVWSYLN  60
RQKKSLLGVD SSSVREQFRI VDRTSDKSGV SHYRLKQYVN GIPVYGAEQT IHVGKSGEVT 120
SYLGAVINED QQEEATQGTT PKISASEAVY TAYKEAAARI EALPTSDDTI SKDAEEPSSV 180
SKDTYAEAAN NDKTLSVDKD ELSLDKASVL KDSKIEAVEA EKSSIAKIAN LQPEVDPKAE 240
LYYYPKGDDL LLVYVTEVNV LEPAPLRTRY IIDANDGSIV FQYDIINEAT GKGVLGDSKS 300
FTTTASGSSY QLKDTTRGNG IVTYTASNRQ SIPGTLLTDA DNVWNDPAGV DAHAYAAKTY 360
DYYKSKFGRN SIDGRGLQLR STVHYGSRYN NAFWNGSQMT YGDGDGDGST FIAFSGDPDV 420
VGHELTHGVT EYTSNLEYYG ESGALNEAFS DVIGNDIQRK NWLVGDDIYT PNICGDALRS 480
MSNPTLYDQP HHYSNLYKGS SDNGGVHTNS GIINKAYYLL AQGGTFHGVT VNGIGRDAAV 540
QIYYSAFTNY LTSSSDFSNA RAAVIQAAKD LYGANSAEAT AAAKSFDAVG             590

SEQ ID NO: 4          moltype = AA  length = 15
FEATURE               Location/Qualifiers
REGION                1..15
```

```
                              note = N-terminal amino acid sequence determined by
                                Takekawa S. et al. J. Bacteriology 173 (1991) 6820-6825
source                        1..15
                              mol_type = protein
                              organism = Bacillus polymyxa 72
VARIANT                       12
                              note = X can be any naturally occurring amino acid.
SEQUENCE: 4
ATGTGKGVLG DXKSF                                                           15

SEQ ID NO: 5                  moltype = AA   length = 592
FEATURE                       Location/Qualifiers
source                        1..592
                              mol_type = protein
                              organism = Paenibacillus polymyxa ATCC21993
SEQUENCE: 5
MKKVWVSLLG GAMLLGSVAS GASAESSVSG PTQLTPTFHA EQWKAPSSVS GDDIVWSYLN    60
RQKKSLLGAD DSSVREQFRI VDRTSDKSGV SHYRLKQYVN GIPVYGAEQT IHVGKSGEVT   120
SYLGAVVTED QQAEATQGTT PKISASEAVY TAYKEAAARI EALPTSDDTI SKDVEEQSSV   180
SKDTYAEAAN NEKTLSTDKD ELSLDKASAL KDSKIEAVEA EKSSIAKIAN LQPEVDPKAD   240
LYFYPKGDDL QLVYVTEVNV LEPAPLRTRY IIDANDGSIV FQYDIINEAT GTGKGVLGDT   300
KSFTTTASGS SYQLKDTTRG NGVVTYTASN RQSIPGTILT DADNVWNDPA GVDAHTYAAK   360
TYDYYKAKFG RNSIDRGLQ  LRSTVHYGSR YNNAFWNGSQ MTYGDGDGST FIAFSGDPDV   420
VGHELTHGVT EYTSNLEYYG ESGALNEAFS DVIGNDIQRK NWLVGDDIYT PNIAGDALRS   480
MSNPTLYDQP DHYSNLYTGS SDNGGVHTNS GIINKAYYLL AQGGTFHGVT VNGIGRDAAV   540
QIYYSAFTNY LTSSSDFSNA RAAVIQAAKD QYGANSAEAT AAAKSFDAVG VN          592

SEQ ID NO: 6                  moltype = DNA   length = 1898
FEATURE                       Location/Qualifiers
misc_feature                  1..1898
                              note = DNA comprising the nucleotide sequence encoding
                                enzymatically active neutral protease from Paenibacillus
                                polymyxa, the DNA having engineered termini facilitating
                                cloning steps
misc_recomb                   5..11
                              note = artificially generated Pae-I restriction cleavage
                                site "GCATGC"
misc_recomb                   1891..1896
                              note = artificially generated Sal-I restriction cleavage
                                site "GTCGAC"
source                        1..1898
                              mol_type = other DNA
                              organism = synthetic construct
CDS                           34..1812
SEQUENCE: 6
gctcgcatgc caaatgagga gagtgaattt ttgatgaaaa aagtatgggt ttcgcttctt     60
ggaggagcta tgttattagg gtctgtcgcg tctggtgcat cagcggagag ttccgtttcg    120
gggccaactc agcttacacc gacctttcac gccgagcaat ggaaagcccc ttcctcggta    180
tcggggggacg acattgtatg gagctatttg aatcggcaaa agaaatcgtt actgggtgcg   240
gacgactcta gtgtacgtga acaattccga atcgttgatc gcacaagcga caagtccggt    300
gtgaaccatt atcggctgaa acagtatgta aacgggattc ccgtatatgg agctgaaccag   360
actattcatg tgggcaaatc tggtgaggtc acctccttact taggagcggt ggttactgag   420
gatcagcaag ctgaagctac gcaaggtaca actccaaaaa tcagcgcttc tgaagcggtc    480
tacactgcat ataagaagc agctgcacgg attgaagccc tccctacctc cgacgatacg    540
atttctaaag atgttgagga acaaagcagt gtaagcaagt acacttacgc cgaagcagct    600
aacaacgaaa aaacgctatc tactgataag gacgagctga gtcttgataa agcatctgcc    660
ctgaaagata gcaaaattga agcggtggaa gcagaaaaaa gttccattgc caaaatcgct    720
aatctgcagc cagaagtaga tccaaaagcc gatctgtact tctatcctaa aggggatgac    780
ctgcagctgg ttttatgtaac agaagtcaat gttttagaac ctgcccccact gcgtactgag   840
tacattattg atgccaatga tggcagcatc gtattccagt atgacatcat taatgaagcg    900
acaggcacag gtaaaggtgt gcttggtgat accaaatcat tcaccacaac tgcttccggc    960
agtagctacc agtaaaaaga tacaaacacgc ggtaacgggg ttgtgaccta cacggcctcc   1020
aaccgtcaaa gcatcccagg taccattctg accgatgccg ataatgtatg gaatgatcca   1080
gccggcgtgg atgcccatac gtatgctgct aaaacatatg attactataa ggccaaattt   1140
ggacgcaaca gcattgacgg acgcgggctg caactccgtt cgacagtcca ttatggtagc   1200
cgttacaaca acgccttctg gaatggctcc caaatgactt atggagacgg ggacggtagc   1260
acatttatcg cattcagcgg ggaccccgat gtggtaggtc atgaacttac gcacggtgtc   1320
acagagtata cttcgaattt ggaatattac ggagagtccc gtgcattgaa tgaggctttc   1380
tcggacgtca tcggtaatga cattcagcgt aaaaattgga ttgtaggcga tgatatttat   1440
acgccaaaca ttgcaggcga tgctctgcgc tctatgtcca atcctaccct gtacgatcaa   1500
ccagatcact attccaactt gtatacaggc agctccgata acgcggcgt tcatacgaac    1560
agcggtatta tcaataaagc ctactatctg ttagcacaag gtggtacttt ccatggcgta   1620
actgtaaatg gaattggccg cgatgcagcg gttcaaattt actatagtgc ctttacgaac   1680
tacctgcctt cttcttccga cttctccaac gcacgcgtgc tgtgatcca agcagcaaaa    1740
gatcagtacg gtgcgaactc agcagaagca actgcagctg ccaaatcttt tgacgctgta   1800
ggcgtaaact aaatcatata cacgatcctc tcattttct gtccatagac ctttgccatt   1860
gtgcaactgt cacttggctc tgccatacca gtcgacgg                            1898

SEQ ID NO: 7                  moltype = AA   length = 592
```

```
FEATURE              Location/Qualifiers
source               1..592
                     mol_type = protein
                     organism = synthetic construct
SEQUENCE: 7
MKKVWVSLLG GAMLLGSVAS GASAESSVSG PTQLTPTFHA EQWKAPSSVS GDDIVWSYLN   60
RQKKSLLGAD DSSVREQFRI VDRTSDKSGV SHYRLKQYVN GIPVYGAEQT IHVGKSGEVT  120
SYLGAVVTED QQAEATQGTT PKISASEAVY TAYKEAAARI EALPTSDDTI SKDVEEQSSV  180
SKDTYAEAAN NEKTLSTDKD ELSLDKASAL KDSKIEAVEA EKSSIAKIAN LQPEVDPKAD  240
LYFYPKGDDL QLVYVTEVNV LEPAPLRTRY IIDANDGSIV FQYDIINEAT GTGKGVLGDT  300
KSFTTTASGS SYQLKDTTRG NGVVTYTASN RQSIPGTILT DADNVWNDPA GVDAHTYAAK  360
TYDYYKAKFG RNSIDGRGLQ LRSTVHYGSR YNNAFWNGSQ MTYGDGDGST FIAFSGDPDV  420
VGHELTHGVT EYTSNLEYYG ESGALNEAFS DVIGNDIQRK NWLVGDDIYT PNIAGDALRS  480
MSNPTLYDQP DHYSNLYTGS SDNGGVHTNS GIINKAYYLL AQGGTFHGVT VNGIGRDAAV  540
QIYYSAFTNY LTSSSDFSNA RAAVIQAAKD QYGANSAEAT AAAKSFDAVG VN          592

SEQ ID NO: 8         moltype = AA  length = 15
FEATURE              Location/Qualifiers
REGION               1..15
                     note = Predicted N-terminal amino acid sequence of Bacillus
                      polymyxa 72 neutral protease
source               1..15
                     mol_type = protein
                     organism = synthetic construct
SEQUENCE: 8
NEATGKGVLG DSKSF                                                    15
```